United States Patent [19]

Quinn

[11] Patent Number: 5,066,674
[45] Date of Patent: Nov. 19, 1991

[54] CARBAMATE INHIBITORS OF CHOLESTEROL ESTERASE AND THEIR USE AS HYPOLIPIDEMIC AND HYPOCALORIC AGENTS

[75] Inventor: Daniel M. Quinn, Iowa City, Iowa

[73] Assignee: University of Iowa Research Foundation, Iowa City, Iowa

[21] Appl. No.: 533,079

[22] Filed: Jun. 4, 1990

[51] Int. Cl.$^5$ .............................................. A61K 31/22
[52] U.S. Cl. ................................... 514/529; 560/134; 560/136; 558/234; 558/235
[58] Field of Search ................. 560/134, 136; 514/529

[56] References Cited

U.S. PATENT DOCUMENTS

| | | | |
|---|---|---|---|
| 3,009,855 | 11/1961 | Lambrech | 560/134 |
| 3,057,910 | 10/1962 | Fischer et al. | 560/134 |
| 3,792,994 | 2/1974 | Baker et al. | 560/136 |
| 4,051,254 | 9/1977 | Maravety | 560/136 |
| 4,095,034 | 6/1978 | Mangold et al. | 560/134 |
| 4,381,195 | 4/1983 | Hyzak | 71/106 |
| 4,786,652 | 11/1988 | Venuti | 560/134 |

OTHER PUBLICATIONS

Hosie, Lynn et al., "p-Nitrophenyl and Cholesteryl-N-Alkyl Carbamates as Inhibitors of Cholesterol Esterase", *Journal of Biological Chemistry*, vol. 262, No. 1, Jan. 5, 1987, pp. 260–264.

Bat, Santhoor G. et al., "The Role of Cholesteryl Ester Hydrolysis and Synthesis in Cholesterol Transport Across Rat Intestinal Mucosal Membrane a New Concept", *Biochem. & Biophys. Res. Comm.*, vol. 109, No. 2, 1982, pp. 486–492.

Gallo, Linda L. et al., "Cholesterol Absorption in Rat Intestine: Role of Cholesterol Esterase and Acyl Coenzyme A: Cholesterol Acyltransferase", *Journal of Lipid Research*, vol. 25, 1984, pp. 604–612.

Watt, Shirley M. et al., "The Effect of Pancreatic Diversion on Lymphatic Absorption and Esterification of Cholesterol in the Rat", *Journal of Lipid Research*, vol. 22, 1982, pp. 157–165.

Sutton, Larry D. et al., "Phenyl-n-Butylborinic Acid is a Potent Transition State Analog Inhibitor of Lipolytic Enzymes", *Biochem & Biophys. Res. Comm.*, vol. 134, No. 1, 1986, pp. 386–392.

*Primary Examiner*—James H. Reamer
*Attorney, Agent, or Firm*—Zarley, McKee, Thomte, Voorhees & Sease

[57] ABSTRACT

Certain carbamate esters are used as inhibitors as cholesterol esterase and function as hypolipidemic and hypocaloric agents. The invention also relates to a method of decreasing the absorption of dietary cholesterol and fats through the wall of the intestinal tract.

10 Claims, 1 Drawing Sheet

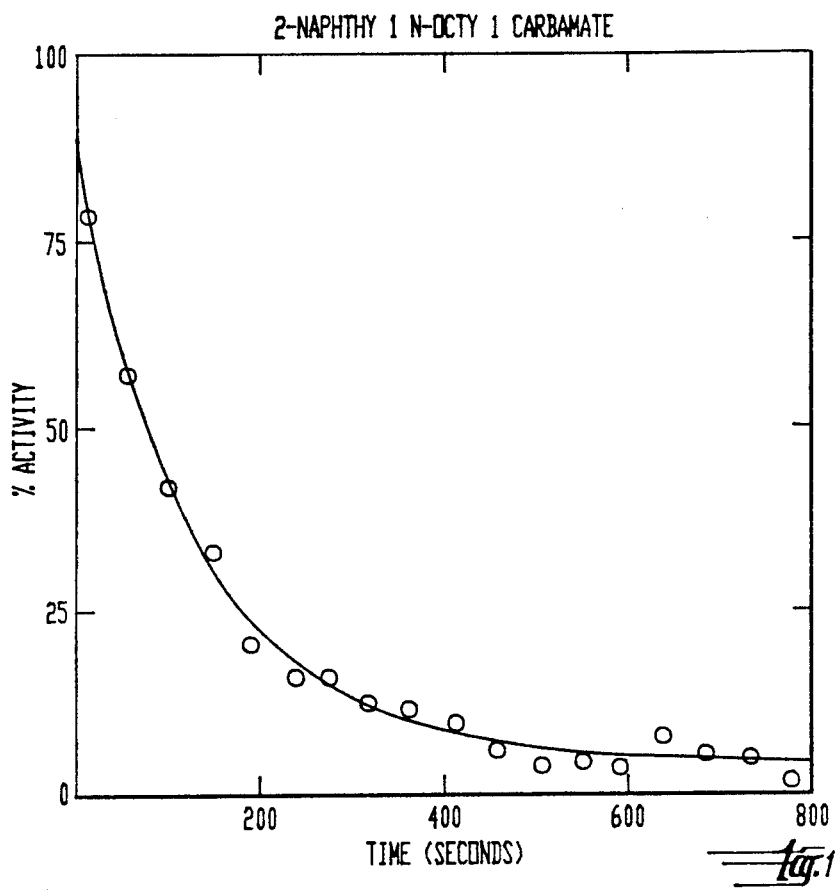
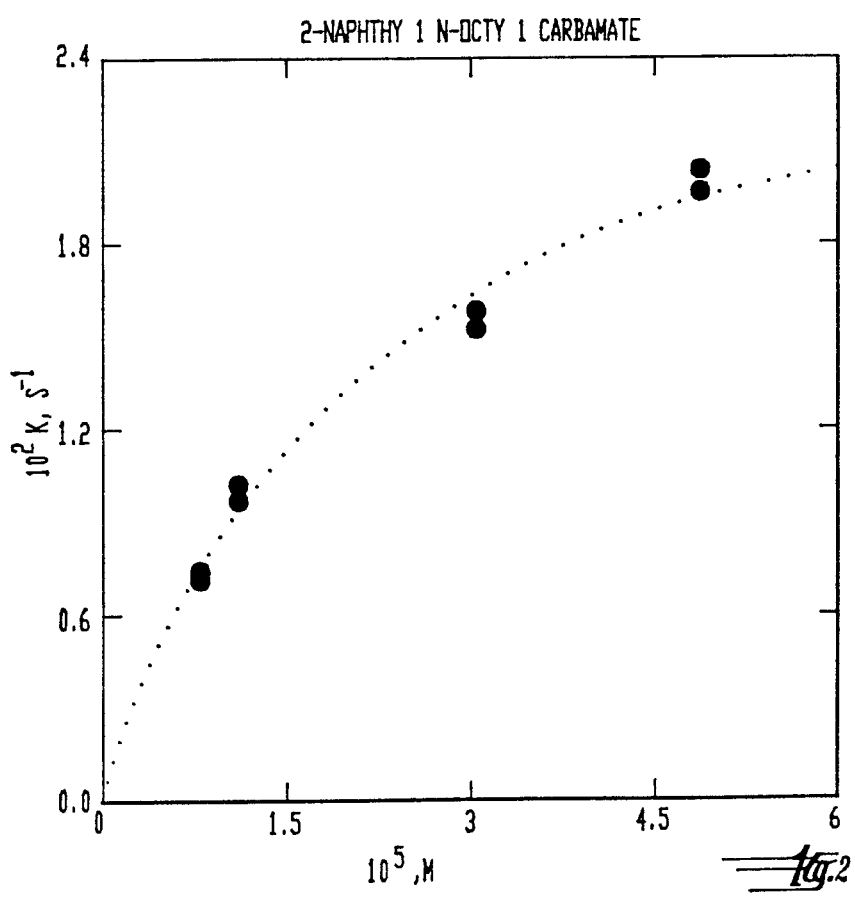

CARBAMATE INHIBITORS OF CHOLESTEROL ESTERASE AND THEIR USE AS HYPOLIPIDEMIC AND HYPOCALORIC AGENTS

GRANT REFERENCE

This invention was made with government support under contract number Hl-30089-B awarded by the National Institutes of Health of the Department of Health and Human services. The Government has certain rights in the invention.

BACKGROUND OF THE INVENTION

Pancreatic cholesterol esterase (CEase) is a lipolytic enzyme that catalyzes the hydrolysis of cholesteryl esters, phospholipids and triacylglycerols in the intestinal tract. The enzyme may play a role in the absorption of dietary cholesterol across the intestinal mucosa and eventually into the bloodstream, though certain literature teaches away from this physiological role, Watt and Simmons, *J. Lioid Res.*, 22, 157-165 (1981). Given the legendary connection between blood serum cholesterol levels and arteriosclerosis, it is reasonable to suspect that reagents that specifically and rapidly inhibit CEase may be worthy of investigation for use in the prophylaxis and/or treatment of the disease. Such agents would be of enormous benefit to the United States and other industrialized societies where atherosclerosis is one of the most prominent causes of death. For example, nearly half of the yearly mortality in the United States results from arteriosclerosis and its sequelae, such as heart attack, stroke, etc. Moreover, the cost to society for surgical and pharmacological management of the disease as well as lost productivity is staggering. It can therefore be seen that there is a continuing, serious and immediate need for development of means of reducing the risk for arteriosclerosis.

One of the often discussed techniques is dietary control. Of course, if diet intake is controlled to reduce the intake of fats, particularly saturated fats, it necessarily follows that the quantity of these materials as absorbed into the blood stream will be decreased. However, such dietary control has proven difficult in modern Western society. Particularly this is true in the United States, where foods are overwhelmingly high in fat content. Thus, for example, in the United States it is generally recognized that high blood cholesterol concentrations provide a significant risk factor in heart disease. It is also generally recognized that the high risk factor for heart disease in the Western world, and particularly the United States is caused by eating foods high in saturated fats, such as many red meats. Accordingly, there is a very real and continuing interest in decreasing either the intake of food substances that have high cholesterol content, or correspondingly in some manner decreasing the absorption rate of the cholesterol and fats through the alimentary tract.

Moreover, since CEase is required for the absorption of dietary fatty acids into the bloodstream, CEase inhibitors may serve as hypocaloric agents (i.e. blockers of the absorption of dietary calories as fat). Such a treatment would be useful in the treatment of obesity, a health problem that afflicts one-third of Americans. It is also a known risk factor in diabetes, atherosclerosis and other life threatening diseases.

It can therefore be seen that there is a real problem, with regard to control of dietary cholesterol. The huge amounts of data documenting the problem suggests the critical need for research and efforts at solving it. There are three possible approaches to lowering blood cholesterol levels for prevention and/or treatment of atherosclerosis: (a) removal of cholesterol from the body; (b) inhibition of de novo cholesterol biosynthesis; (c) prevention of absorption of dietary cholesterol. The first two approaches have been used commercially with some degree of success. For example, the drug Questeran ®, which contains the cationic resin cholestyramine, is marketed by Bristol-Myers and lowers blood cholesterol by binding to bile salts in the intestinal lumen. The complex of Questran ® and bile salts is eliminated in the feces, and the liver responds to the loss of bile salts by increasing receptor-mediated uptake of cholesterol ester-rich lipoproteins from the bloodstream. In 1988 Merck, Sharp and Dohme began marketing the HMG-CoA reductase inhibitor Mevacor ®, which prevents cholesterol biosynthesis in the liver. While these efforts are steps along the way, there remains a continuing need for further treatments and approaches.

The third approach, i.e., prevention of absorption of dietary cholesterol, has been largely unexploited as a pharmacological method for treatment of atherosclerosis. One way of prevention of absorption of dietary cholesterol is to cover the walls of the intestinal tract with something which prevents absorption of dietary cholesterol through the intestinal mucosa. This, however, is difficult and not practical because it inhibits the normal digestive process. A far more effective approach would be to develop CEase inhibitors with demonstrated capability of blocking cholesterol absorption. These inhibitors could then be introduced into the alimentary tract through appropriate delivery systems where it would then function to block cholesterol absorption. This invention is predicated upon the discovery of certain novel CEase inhibitors to successfully block cholesterol absorption, to their use for decreasing the absorption of dietary cholesterol and other fats, and to a pharmaceutical composition comprising the active compound in unit dosage formulations.

BRIEF DESCRIPTION OF THE DRAWINGS

FIG. 1 shows a timecourse for inhibition of CEase by 2-naphthyl n-octylcarbamate.

FIG. 2 shows a non-linear least squares fit of data from FIG. 1 to equation (2) set forth below.

SUMMARY OF THE INVENTION

Carbamate esters of the formula:

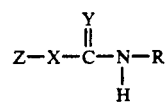

wherein Z equals an aryl moiety selected from the group consisting of 2-naphthyl and p-acetamidophenyl, and X and Y are either oxygen or sulfur, and R is a $C_1$ to $C_8$ alkyl are prepared. These are encapsulated in a dose delivery system and administered to decrease the absorption of dietary cholesterol through the intestinal tract. The new compounds have not only been discovered to be cholesterol esterase inhibitors, but this property for these compounds, surprisingly, directly correlates with decreasing the rate of absorption of dietary cholesterol.

DETAILED DESCRIPTION OF THE INVENTION

This invention relates to aryl carbamates that are irreversible inhibitors of CEase. Because of the role of CEase in absorption of dietary fats, including cholesterol, these compounds represent a new approach to the design of hypolipidemic and hypocaloric agents. Moreover, in view of the teaching of current literature such as the cited Watt & Simmons article, it is surprising that these compounds function to decrease absorption of dietary cholesterol. Another advantage of the CEase inhibitors of this invention is that they are poorly absorbed into the bloodstream and they are resistant to CEase-catalyzed hydrolysis. Therefore, they pass through the intestinal tract unchanged. And, excess inhibitor should be eliminated in the feces; thus, the problems that attend absorption and systemic distribution should be largely avoided.

To accomplish these advantages, the carbamate inhibitors that are described in this invention are designed as structural biomimics of cholesteryl esters. As a result effective dietary cholesterol blockage is achieved with active CEase inhibitors which themselves offer minimum side effect risk when administered.

Compounds useful as CEase inhibitors of this invention are novel carbamate esters of the formula:

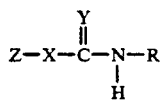

wherein Z equals an aryl moiety selected from the group consisting of 2-naphthyl and p-acetamidophenyl. Where Z is 2-naphthyl, an additional substituted moiety W may attach to the polynuclear ring as below illustrated.

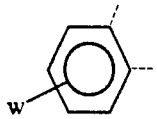

W may be selected from the group of $C_1$ to $C_8$ alkyl, halides, and OR, wherein R is as below described.

Turning back to the general formula for the carbamate esters, X and Y may be the same or different, and are selected from the group of oxygen and sulfur. R is defined as $C_1$ to $C_8$ alkyl, preferably $C_4$ to $C_8$ alkyl. It is preferred that Z be 2-naphthyl, X and Y are both oxygen. These preferred compounds have been found to be most effective CEase inhibitors and correspondingly the most effective dietary cholesterol absorption blockers.

In order to decrease the dietary absorption of cholesterol, fats, phospholipids, etc., the compounds of the present invention must be administered in a small but effective cholesterol esterase inhibiting amount. The usual method of administration is orally into the alimentary tract in a unit dosage form. In such systems, the active compound is combined with a pharmaceutical carrier, with the active compound dosed to provide a level ranging from 0.01 mg to about 1.0 mg per kg of body weight.

Pharmaceutical carriers which are acid resistant to the acid pH of the stomach (normally is about 2) may be used. They also should be nondigestable to the enzyme pepsin which is present in the stomach. There are commercially available solid pharmaceutical carriers which are resistant to stomach degradation and will pas through to the small intestine where the bile in the intestine which is more lipophilic will dissolve them. See for example Viokase and Entozyme that are marketed by A.H. Robins Company of Richmond, Va. These compounds are examples of carriers that dissolve in the small intestine but not in the stomach. Another potential coating is marketed by Lactaid, Inc. of Pleasantville, N.J. The preferred carriers are solid carrier materials, and flavor materials may be added to those.

Solid pharmaceutical carriers such as starch, sugar, talc, mannitol and the like may be used to form powders. Mannitol is the preferred solid carrier. The powders may be used as such for direct administration or, instead, the powders may be added to suitable foods and liquids, including water, to facilitate administration.

The powders also may be used to make tablets, or to fill gelatin capsules. Suitable lubricants like magnesium stearate, binders such as gelatin, and disintegrating agents like sodium carbonate in combination with citric acid may be used to form the tablets.

Unit dosage forms such as tablets and capsules may contain any suitable predetermined amount of the active carbamate ester and may be administered one or more at a time at regular intervals. Such unit dosage forms, however, should generally contain a concentration of 0.1% to 10% by weight of the tablet of one or more of the active compounds.

A typical tablet may be the composition:

|   | Mg. |
|---|---|
| 1. Active carbamate ester | 12.5 |
| 2. Mannitol | 100 |
| 3. Stearic acid | 3 |

A granulation is made from the mannitol. The other ingredients are added to the dry granulation and then the tablets are punched.

Another tablet may have the compositions:

|   | Mg. |
|---|---|
| 1. Active carbamate ester | 10 |
| 2. Starch U.S.P. | 57 |
| 3. Lactose U.S.P. | 73 |
| 4. Talc U.S.P. | 9 |
| 5. Stearic acid | 6 |

Powders 1, 2 and 3 are slugged, then granulated, mixed with 4 and 5, and tableted.

Capsules may be prepared by filling No. 3 hard gelatin capsules with the following ingredients, thoroughly mixed:

|   | Mg. |
|---|---|
| 1. Active carbamate ester | 5 |
| 2. Lactose U.S.P. | 200 |
| 3. Starch U.S.P. | 16 |
| 4. Talc U.S.P. | 8 |

As earlier explained, there are certain of the compounds falling within the general formula which are preferred. The preferred compounds have been selected on the basis of structure reactivity studies. Generally, those which are most preferred are those which have a straight alkyl chain of six to eight carbons in length, coupled with a fused ring system of at least two rings. The method of preparation of these compounds involves fairly routine synthesis procedures, known to those of skill in organic synthesis. However, the scheme for synthesizing these compounds is set forth below.

SCHEME

SCHEME

1) Isocyanate Synthesis

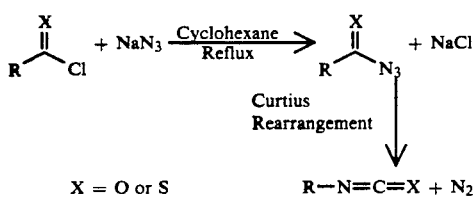

$$X = O \text{ or } S \qquad R-N=C=X + N_2$$

2) Carbamate Synthesis

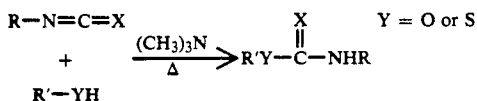

Generally speaking, the procedure as above outlined involves two steps. In step 1, the appropriate acid chloride as illustrated is converted to an acyl azide with sodium azide and refluxing cyclohexane. The acyl azide undergoes the Curtius rearrangement in situ to the corresponding isocyanate. In the second step described in the scheme as the carbamate synthesis, isocynate and phenol (i.e. p-acetamidophenol, 2-naphthol, unbelliferone) or chloresterol are reacted in the presence of trimethylamine to form the desired carbamate.

The following examples are offered to further illustrate but not limit the scope of the present invention. It should be understood that reasonable modifications, both the processes and the compounds, can be made without departing from the scope and spirit of the invention, and those reasonable modifications are intended to be included within the scope of the present invention.

EXAMPLES

Using the two-step procedure outlined in the scheme illustrated above, the five CEase carbamate inhibitors listed in Table I below were prepared, and their structures confirmed. Operation conditions for each varied in only minor aspects. The first reaction consisted of two phases and utilized a 2:1 ratio of sodium azide in the lower aqueous and acid chloride in the upper cyclohexane phase; and then the upper phase was removed and refluxed for 1.5 hours at 70° C. The second reaction involving the carbamate synthesis was conducted using equimolar quantities and heating at a temperature of 70° C.

The CEase-catalyzed hydrolysis of the water-soluble substrate p-nitrophenyl butyrate (PNPB) is the reaction that was routinely used to characterize irreversible inhibitors. The reaction is followed at 25.0±0.1° C. and pH 7.3 in 0.1M sodium phosphate buffer that contains 0.1N NaCl, 1 mM Triton X100, and the appropriate concentrations of CEase and PNPB. Characterization of inhibitors occurs in three steps: First, inhibitor is added to CEase and the percent activity of the enzyme is measured as a function of time. A corresponding control (contains no inhibitor) measures the 100% activity level. Secondly, the pseudo-first order inhibition rate constant is calculated from the activity versus time data.

$$\%A = (\%A_O - \%A_{inf})e^{-kt} + \%A_{inf} \qquad (1)$$

FIG. 1 shows a fit to equation 1 of a timecourse for inhibition of CEase by 2-naphthyl n-octyl carbamate. The pseudofirst order inhibition rate constant is plotted versus [I]. If the plot is linear, the second-order inhibition rate constant, $k_i/K_i$, is the slope of a linear-least squares fit of the plot. And, thirdly, if plot is nonlinear and hyperbolic, the following inhibition mechanism is indicated:

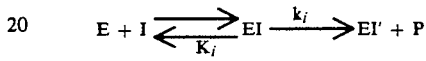

In this mechanism, the inhibitor first forms a reversible, noncovalent complex, EI, with the enzyme. An enzymic nucleophile, presumably the active site serine (cf. Scheme I) then attacks the carbonyl carbon of the carbamate functionality of the inhibitor, with subsequent expulsion of the aromatic leaving group. For the above mechanism, the dependence of k on [I] is described by the following equation:

$$k = \frac{K_i[I]}{K_i + [I]} \qquad (2)$$

FIG. 2 shows a nonlinear-least squares fit of data to equation 2 for inhibition of CEase by 2-naphthyl n-octyl carbamate. From this fit the maximum first-order inhibition rate constant ($k_i$) and the dissociation constant of EI ($K_i$) were determined, and consequently $k_i/K_i$ could be calculated.

Table I lists second-order inhibition rate constants for the inhibitors that have been evaluated to date. These data show the 2-naphthyl n-octyl carbamate is the most potent irreversible carbamate inhibitor of CEase.

TABLE I

Second-Order Inhibition Rate Constants for Carbamate Inhibitors of Cholesterol Esterase

| Inhibitor | $k_i/K_i$, $M^{-1}s^{-1}$ | $t_{\frac{1}{2}}$, min[a] |
|---|---|---|
| 2-Naphthyl n-Octyl Carbamate | 1350 | 0.86 |
| p-Acetamidophenyl n-Butyl Carbamate | 40 | 29 |
| p-Acetamidophenyl n-Pentyl Carbamate | 100 | 11.6 |
| p-Acetamidophenyl n-Hexyl Carbamate | 493 | 2.3 |
| p-Acetamidophenyl n-Octyl Carbamate | 100 | 11.6 |

[a]Half-life of irreversible inhibition in presence of $10^{-5}$M inhibitor; calculated according to $t_{\frac{1}{2}} = \ln(2)/(k_i[I])$, where [I] is the inhibitor concentration.

The date presented in Table I shows that the carbamate esters of the present invention are useful irreversible inhibitors of CEase. The data indicates the compounds to be useful as CEase inhibitors in animals, and absorption blockers for dietary cholesterol and fats.

In sum, it therefore can be seen as illustrated by the specification, the drawings, and the examples, that applicant has provided a group of highly useful carbamate esters having utility as effective CEase inhibitors which can be used to effectively decrease the rate and amount of absorption of dietary cholesterol.

What is claimed is:

1. A method of decreasing the absorption of dietary cholesterol and fats through the wall of the intestinal tract, said method comprising:

administering to a mammal a small but cholesterol esterase inhibiting effective amount of a compound of the formula:

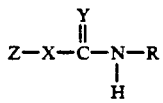

wherein Z equals an aryl moiety selected from the group consisting of 2-naphthyl and p-acetamidophenyl, X and Y are oxygen, and R is a $C_1$ to $C_8$ alkyl.

2. A carbamate ester of claim 1 wherein Z is 2-naphthyl.

3. A carbamate ester of claim 2 wherein an additional moiety W is attached to said 2-naphthyl, and W is selected from the group consisting of $C_1$ to $C_8$ alkyl, halides and $C_1$ to $C_8$ oxyalkyl.

4. A compound of claim 3 wherein R is $C_1$ to $C_8$ alkyl.

5. A compound of claim 3 wherein R is $C_4$ to $C_8$ alkyl.

6. A unit dosage pharmaceutical composition comprising a pharmaceutical carrier and from 0.01 mg to 1.0 mg/kg of body weight of a carbamate ester of the formula:

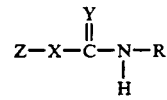

wherein Z equals an aryl moiety selected from the group consisting of 2-naphthyl and p-acetamindophenyl, X and & are oxygen, and R is a $C_1$ to $C_8$ alkyl.

7. A carbamate ester of claim 6 wherein Z is 2-naphthyl.

8. A carbamate ester of claim 7 wherein an additional moiety W is attached to said 2-naphthyl, and W is selected from the group consisting of $C_1$ to $C_8$ alkyl, halides and $C_1$ to $C_8$ oxyalkyl.

9. A compound of claim 8 wherein R is $C_1$ to $C_8$ alkyl.

10. A compound of claim 8 wherein R is $C_4$ to $C_8$ alkyl.

* * * * *